(12) United States Patent
Jungnickel et al.

(10) Patent No.: US 9,370,409 B2
(45) Date of Patent: Jun. 21, 2016

(54) ELECTRO-POLYMER MOTOR

(71) Applicant: Braun GmbH (a German Corporation), Kronberg (DE)

(72) Inventors: Uwe Jungnickel, Taunus (DE); Benedikt Heil, Hesse (DE)

(73) Assignee: BRAUN GMBH, Kronberg (DE)

( * ) Notice: Subject to any disclaimer, the term of this patent is extended or adjusted under 35 U.S.C. 154(b) by 728 days.

(21) Appl. No.: 13/705,344

(22) Filed: Dec. 5, 2012

(65) Prior Publication Data
US 2013/0091643 A1 Apr. 18, 2013

Related U.S. Application Data

(62) Division of application No. 12/544,303, filed on Aug. 20, 2009, now Pat. No. 8,350,447.

(60) Provisional application No. 61/090,306, filed on Aug. 20, 2008.

(51) Int. Cl.
| | |
|---|---|
| *H02N 2/10* | (2006.01) |
| *A61C 17/22* | (2006.01) |
| *A46B 15/00* | (2006.01) |
| *A61C 17/34* | (2006.01) |
| *H01L 41/09* | (2006.01) |

(52) U.S. Cl.
CPC .............. *A61C 17/22* (2013.01); *A46B 15/0002* (2013.01); *A46B 15/0006* (2013.01); *A46B 15/0008* (2013.01); *A61C 17/34* (2013.01); *A61C 17/3418* (2013.01); *A61C 17/3463* (2013.01); *A61C 17/3472* (2013.01); *H02N 2/10* (2013.01); *A46B 2200/1066* (2013.01); *A61C 17/221* (2013.01); *H01L 41/0986* (2013.01)

(58) Field of Classification Search
CPC ......... H02N 2/001; H02N 2/002; H02N 2/02; H02N 2/04; H02N 2/046
USPC .................. 310/323.01–323.21, 328
See application file for complete search history.

(56) References Cited

U.S. PATENT DOCUMENTS

| | | | |
|---|---|---|---|
| 5,165,131 A | * | 11/1992 | Staar ............................ 15/22.1 |
| 6,376,971 B1 | | 4/2002 | Pelrine et al. |
| 6,543,110 B1 | | 4/2003 | Pelrine et al. |

(Continued)

FOREIGN PATENT DOCUMENTS

| | | |
|---|---|---|
| CA | 2 670 685 | 7/2008 |
| WO | WO 01/80284 A2 | 10/2001 |

(Continued)

*Primary Examiner* — Derek Rosenau
(74) *Attorney, Agent, or Firm* — Vladimir Vitenberg

(57) ABSTRACT

An electro-polymer motor comprising a fixed member and a first actuator having a first end fixedly connected to the fixed member and a second end is presented. The first actuator comprises a polymer positioned between two electrodes. The electrodes are in communication with a power supply. The motor also comprises a driven member comprising a first leg and a second leg such that the first leg and the second leg are separated by an axis. The driven member is fixedly connected to the second end of the first actuator. The motor also comprises a compressible member having a first end fixedly connected to the fixed member and a second end fixedly connected to the second leg of the driven member. The compressible member is spaced apart from the first actuator. The first actuator elongates after the power supply applies a voltage across the electrodes to move the driven member.

12 Claims, 14 Drawing Sheets

(56) References Cited

U.S. PATENT DOCUMENTS

| | | |
|---|---|---|
| 6,545,384 B1 | 4/2003 | Pelrine et al. |
| 6,583,533 B2 | 6/2003 | Pelrine et al. |
| 6,586,859 B2 | 7/2003 | Kornbluh et al. |
| 6,628,040 B2 | 9/2003 | Pelrine et al. |
| 6,664,718 B2 | 12/2003 | Pelrine et al. |
| 6,707,236 B2 | 3/2004 | Pelrine et al. |
| 6,768,246 B2 | 7/2004 | Pelrine et al. |
| 6,781,284 B1 | 8/2004 | Pelrine et al. |
| 6,806,621 B2 | 10/2004 | Heim et al. |
| 6,809,462 B2 | 10/2004 | Pelrine et al. |
| 6,812,624 B1 | 11/2004 | Pei et al. |
| 6,876,135 B2 | 4/2005 | Pelrine et al. |
| 6,882,086 B2 | 4/2005 | Kornbluh et al. |
| 6,891,317 B2 | 5/2005 | Pei et al. |
| 6,911,764 B2 | 6/2005 | Pelrine et al. |
| 6,940,211 B2 | 9/2005 | Pelrine et al. |
| 7,034,432 B1 | 4/2006 | Pelrine et al. |
| 7,049,732 B2 | 5/2006 | Pei et al. |
| 7,064,472 B2 | 6/2006 | Pelrine et al. |
| 7,166,953 B2 | 1/2007 | Heim et al. |
| 7,199,501 B2 | 4/2007 | Pei et al. |
| 7,211,937 B2 | 5/2007 | Kornbluh et al. |
| 7,224,106 B2 | 5/2007 | Pei et al. |
| 7,233,097 B2 | 6/2007 | Rosenthal et al. |
| 7,237,524 B2 | 7/2007 | Pelrine et al. |
| 7,240,655 B2 | 7/2007 | Pelrine et al. |
| 7,259,503 B2 | 8/2007 | Pei et al. |
| 7,320,457 B2 | 1/2008 | Heim et al. |
| 7,362,032 B2 | 4/2008 | Pelrine et al. |
| 7,368,862 B2 | 5/2008 | Pelrine et al. |
| 7,378,783 B2 | 5/2008 | Pelrine et al. |
| 7,394,182 B2 | 7/2008 | Pelrine et al. |
| 7,411,332 B2 | 8/2008 | Kornbluh et al. |
| 7,436,099 B2 | 10/2008 | Pei et al. |
| 7,456,549 B2 | 11/2008 | Heim et al. |
| 7,498,926 B2 | 3/2009 | Browne et al. |
| 7,538,445 B2 | 5/2009 | Kornbluh et al. |
| 7,557,456 B2 | 7/2009 | Kornbluh et al. |
| 7,567,681 B2 | 7/2009 | Pelrine et al. |
| 7,608,989 B2 | 10/2009 | Heydt et al. |
| 2004/0124738 A1 | 7/2004 | Pelrine et al. |
| 2008/0022517 A1 | 1/2008 | Rosenthal |

FOREIGN PATENT DOCUMENTS

| | | |
|---|---|---|
| WO | WO 02/071592 A2 | 9/2002 |
| WO | WO 2006/102273 A2 | 9/2006 |
| WO | WO 2007/097763 A1 | 8/2007 |
| WO | WO 2007/100606 A2 | 9/2007 |

* cited by examiner

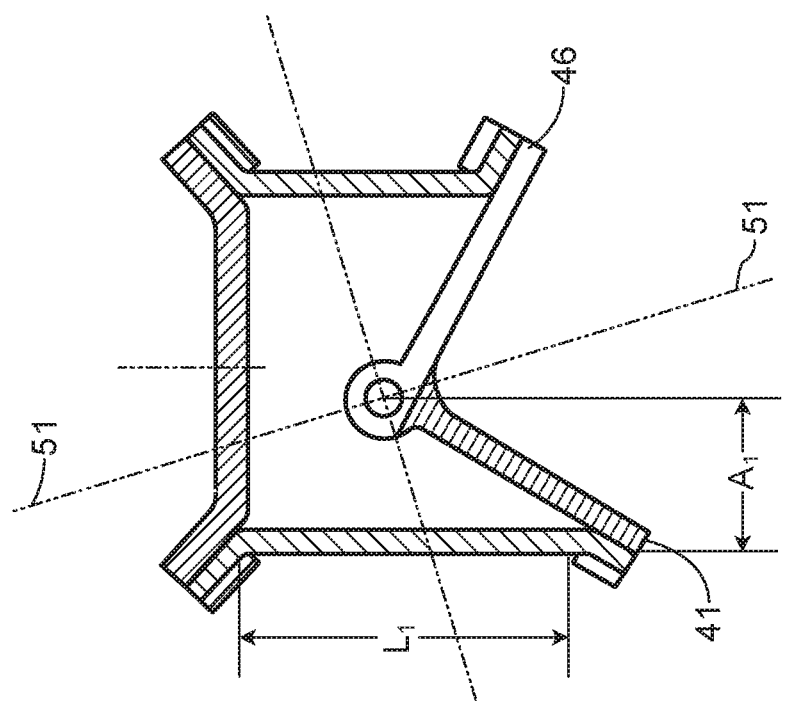
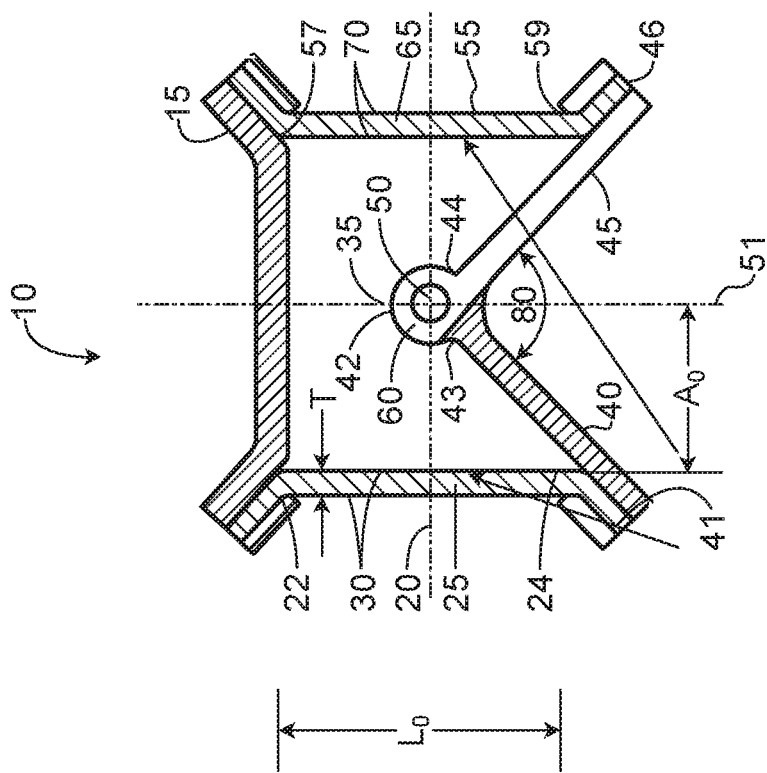
Fig. 1A
Fig. 1B

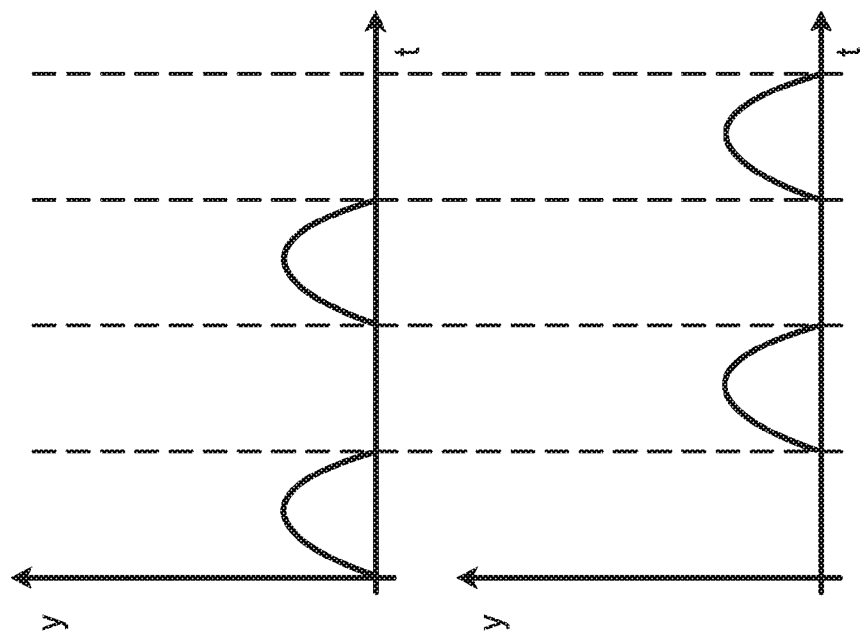
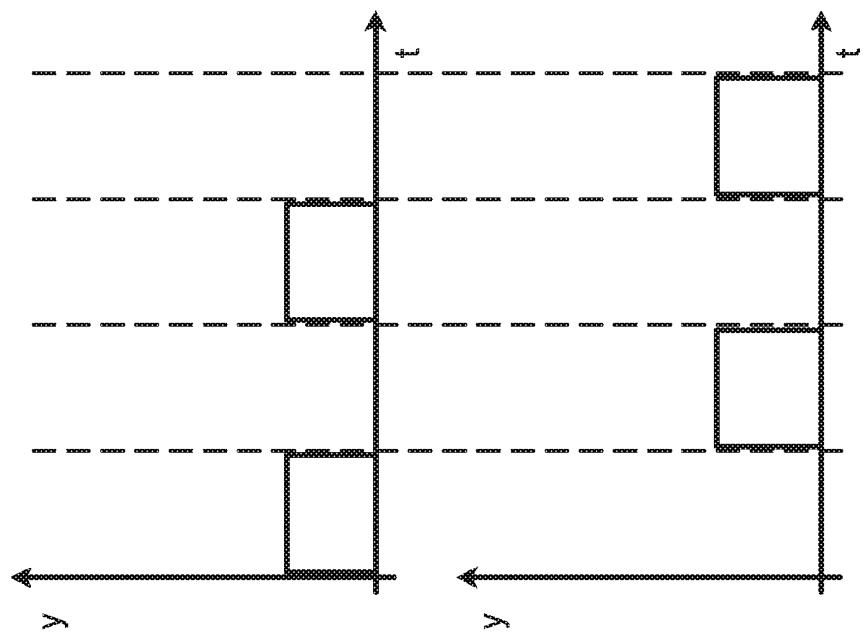
Fig. 4B
Fig. 4A

ELECTRO-POLYMER MOTOR

BACKGROUND OF THE INVENTION

The present invention relates, generally, to electro-polymer motors and, in particular, relates to electro-polymer motors that oscillate and/or pulsate a driven member in small appliances.

Electro-polymer motors typically have been used in robotics, lens-positioning and in pumps. Generally, these motors comprise a layer of polymer film situated between two conductive and elastic layers (i.e., electrodes). The polymer can be thought of as a dielectric. The polymer deforms in response to a voltage that is applied across the pair of electrodes, thereby, converting electrical power to mechanical movement.

SUMMARY OF THE INVENTION

According to the present invention, an electro-polymer motor comprising a fixed member and a first actuator having a first end fixedly connected to the fixed member and a second end is presented. The first actuator may comprise a polymer positioned between two electrodes. The electrodes may be in communication with a power supply. The motor also may comprise a driven member comprising a first leg and a second leg such that the first leg and the second leg may be separated by an axis. The driven member may be fixedly connected to the second end of the first actuator. The motor also may comprise a compressible member having a first end fixedly connected to the fixed member and a second end fixedly connected to the second leg of the driven member. The compressible member may be spaced apart from the first actuator. The first actuator may elongate after the power supply applies a voltage across the electrodes to move the driven member.

In accordance with another embodiment of the present invention, the polymer may be pre-strained.

In accordance with another embodiment of the present invention, the first leg of the driven member and the second leg of the driven member may be separated by a first angle across a central axis.

In accordance with yet another embodiment of the present invention, an electric toothbrush comprises a head having a cleaning surface and a handle connected to the head is presented. The handle may have a power supply and a motor. The motor may comprise a first actuator having a first end fixedly connected to the handle and a second end. The first actuator may comprise a pre-strained polymer positioned between two electrodes. The electrodes may be in communication with the power supply. The motor also may comprise a second actuator having a first end fixedly connected to the handle and a second end. The second actuator may be spaced apart from and substantially parallel to the first actuator. The second actuator may comprise a pre-strained polymer positioned between two electrodes that may be in communication with the power supply. The toothbrush also may comprise a driven member comprising a first leg, a second leg and a shaft bearing positioned between and connected to the first leg and the second leg such that the first leg and the second leg may be separated by a first angle across the shaft bearing. The first leg may be connected to the second end of the first actuator and the second leg may be connected to the second end of the second actuator. Finally, the toothbrush may comprise a shaft in communication with the shaft bearing of the driven member. The first and second actuators may elongate in response to an applied voltage from the power supply to oscillate, pulsate and/or linearly move the driven member and the shaft.

In accordance with still another embodiment of the present invention, a method of electro-polymer motion is presented. The method may comprise alternately actuating a first pre-strained polymer actuator and a second pre-strained polymer actuator with a oscillating pulse from a power supply and oscillating a driven member by the actuation of the first and second actuators about an axis of the driven member.

In accordance with still yet another embodiment of the present invention, the power supply may supply a substantially concurrent pulsating pulse between the alternating oscillating pulses to produce substantially concurrent oscillating and pulsing motion of the driven member about the central axis.

Accordingly, it is a feature of the embodiments of the present invention to provide an electro-polymer motors in small appliances, such that the small appliances have the potential of being more cost-effective, lightweight, consume less power, and smaller. Other features of the embodiments of the present invention will be apparent in light of the description of the invention embodied herein.

BRIEF DESCRIPTION OF THE DRAWINGS

The following detailed description of specific embodiments of the present invention may be best understood when read in conjunction with the following drawings, where like structure is indicated with like reference numerals and in which:

FIG. 1A illustrates a schematic representation of an exemplary electro-polymer motor according to another embodiment of the present invention;

FIG. 1B illustrates a schematic partially rotated representation of the exemplary electro-polymer motor according to FIG. 1A;

FIG. 4A illustrates an exemplary digital oscillating voltage pattern according to an embodiment of the present invention;

FIG. 4B illustrates an exemplary sinusoid oscillating voltage pattern according to an embodiment of the present invention;

Figure 2:
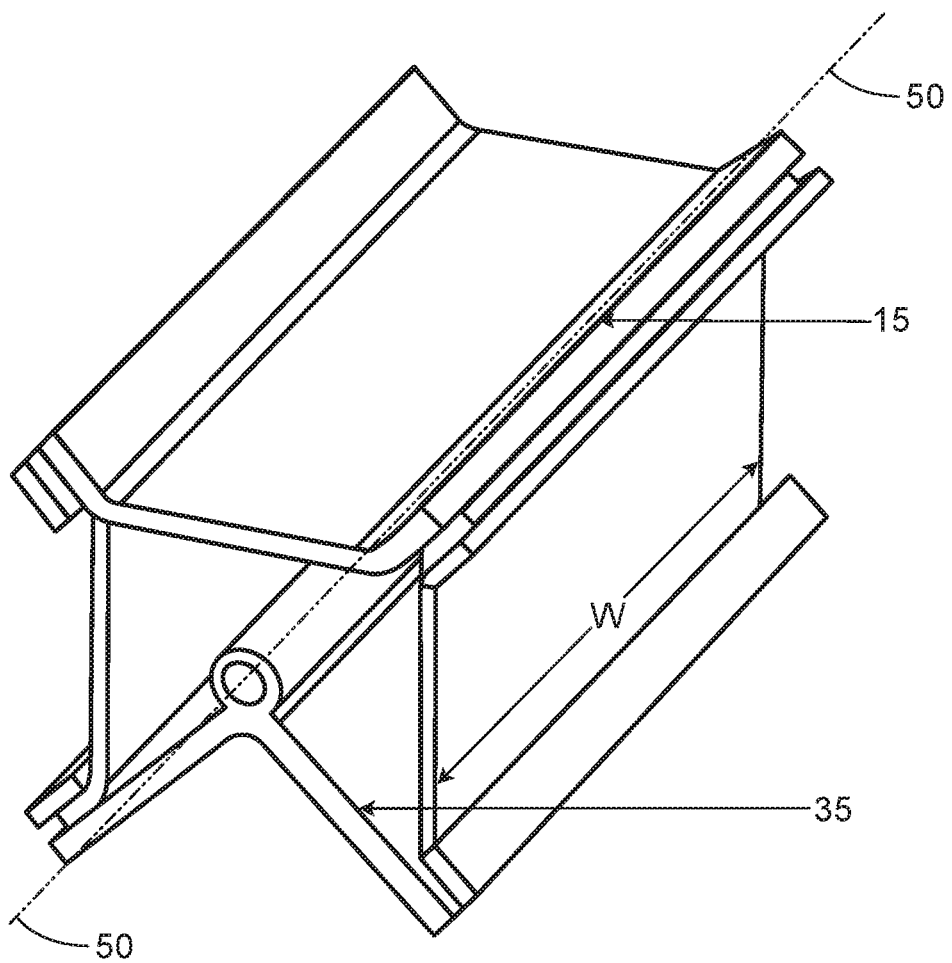
FIG. 2 illustrates a perspective representation of an exemplary toothbrush according to an embodiment of the present invention.

The embodiments set forth in the drawings are illustrative in nature and not intended to be limiting of the invention defined by the claims. Moreover, individual features of the drawings and the invention will be more fully apparent and understood in view of the detailed description

DETAILED DESCRIPTION

The following text sets forth a broad description of numerous different embodiments of the present invention. The description is to be construed as exemplary only and does not describe every possible embodiment since describing every possible embodiment would impractical, if not impossible, and it will be understood that any feature, characteristic, structure, component, step or methodology described herein can be deleted, combined with or substituted for, in whole or part, any other feature, characteristic, structure, component, product step or methodology describe herein. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . ." or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential to the present invention unless so stated. Unless a claim element is defined by reciting the word "means" and a function without the recital of any structure, it is not intended that the scope of any claim element be interepreted based on the application of 35 U.S.C. §112, sixth paragraph.

In the following detailed description of the embodiments, reference is made to the accompanying drawings that form a part hereof, and in which are shown by way of illustration, and not by way of limitation, specific embodiments in which the invention may be practiced. It is to be understood that other embodiments may be utilized and that logical, mechanical and electrical changes may be made without departing from the spirit and scope of the present invention.

Referring initially to FIG. 1A, a schematic representation of an exemplary electro-polymer motor 10 is illustrated. The exemplary electro-polymer motor 10 may comprise a driven member 35, a first actuator 20 connected between the driven member 35 and a fixed member 15, and a compressible member 55 connected between the driven member 35 and the fixed member 15. The fixed member 15 may optionally be part of the motor 10 or be a component separate from the motor 10 such as, for example, a handle of a toothbrush (e.g., the handle 180 as shown in greater detail in FIGS. 7-10).

The driven member 35 may comprise a central body 42, a first leg 40 extending from the central body 42, and a second leg 45 extending from the central body 42 opposite the first leg. The first leg 40 and second leg 45 may be symmetrically about a central plane 51. The central body 42 may be disposed longitudinally along a longitudinal axis 50 of the motor 10, as seen in FIG. 2. The second leg 45 may be disposed radially about the longitudinal axis 50 at an first angle 80 from the first leg 40. The angle 80 may be between about 0 degrees to about 360 degrees, from about 30 degrees to about 180 degrees, or from about 45 degrees to about 90 degrees. The driven member 35 may rotate clockwise and/or counter clockwise about the longitudinal axis 50.

The central body 42 in this exemplary embodiment may comprise a substantially cylindrical shape having a cylindrical shaped aperture 60 disposed therethrough and coaxially-aligned with the longitudinal axis 50. As such, the aperture 60 may be slid onto and attached to a drive shaft of a small appliance such as a toothbrush. The aperture 60 may also comprise a shaft bearing (not shown) as known to one of ordinary skill in the art. In an alternative embodiment, the central body 42 may integrally form a portion of a drive shaft for a small appliance such as a toothbrush or be connected to such a drive shaft. In another exemplary embodiment, illustrated in FIG. 3, the first leg 40 and second leg may be substantially linearly aligned such that the first angle may be substantially 180 degrees. It is understood that the first and second legs may comprise an integral unit.

The first leg 40, second leg 45, and central body 42 may all be a single, integral component or may be three separate and distinct components connected together using known means and methods to form the driven member 35. As shown in FIG. 1A, the first leg 40 may comprise a proximal end 43 adjacent to the central body 42 and a distal end 41 opposite the proximal end. Similarly, the second leg 45 may comprise a proximal end 44 adjacent to the central body and a distal end 46 opposite the proximal end.

The distal end 41 of the first leg 40 may be fixedly connected to a second end 24 of the first actuator 20 using a variety of known and unknown connection methods and devices, including but not limited to welds, sonic welds, adhesives, seaming technologies, brackets, laminating technologies and methods, combinations thereof, or the like. Although, shown connected to the distal end 41 of the first leg 40, it is understood that the first actuator 20 may be connected anywhere along the length and/or width of the first leg 40. A first end 22 of the first actuator 20 may be fixedly connected to fixed member 15 using a variety of known and unknown connection methods and devices, including but not limited to welds, sonic welds, adhesives, seaming technologies, brackets, laminating technologies and methods, combinations thereof, or the like.

As shown in FIG. 1A, the first actuator 20 may comprise a polymer 25 positioned between a pair of electrodes 30. The pair of electrodes 30 may be attached to the opposite surfaces of the first actuator 20 in a variety of known ways, including but not limited to adhesives, sonic welds, mechanical connectors, coatings, combinations thereof, and the like. The pair of electrodes 30 may be in communication with a power supply (not shown). The pair of electrodes 30 may apply a voltage across the polymer 25 resulting in the polymer 25 deforming (i.e., the polymer 25 may expand and/or contract in response to the applied voltage) in a multitude of different directions (i.e., lengthwise, widthwise, diagonally, etc.). Polymers 25 and electrodes 30 suitable for use in the present invention are further described in U.S. Patent Nos. 6,545,384 and 6,781,284, which are herein incorporated by reference for all purposes.

The first actuator 20 may have a length (L) from about 0.1 mm to about 200 mm, more specifically, the first actuator 20 may have a length from about 0.5 mm to about 150 mm and even more specifically first actuator 20 may have a length from about 1 mm to about 100 mm The first actuator 20 may have a width from about 0.1 mm to about 80 mm, more specifically, the first actuator 20 may have a width from about 0.5 mm to about 60 mm and even more specifically first actuator 20 may have a width from about 1 mm to about 40 mm A single actuator 20 may have a thickness from about 1 μm to about 200 μm, more specifically a single actuator 20 may have a thickness from about 3 μm to about 150 μm, and even more specifically a single actuator 20 may have a thickness from about 5 μm to about 100 μm. In another exemplary embodiment, more than one polymer 25 may be laminated together to produce greater force for displacement. In this embodiment, the laminated polymers may have an overall thickness from about 2 μm to about 20 mm, more specifically, the laminated polymers may have an overall thickness from about 20 μm to about 5 mm, and even more specifically, the laminated polymers may have an overall thickness of about 1 mm In one embodiment, the polymer 25 in the actuator 20 may be pre-strained. In one embodiment, the actuator 20 may be pre-strained by about 0.1 to 60%. In another embodiment, the actuator 20 may be pre-strained by 2 to 20%. In still another embodiment, the actuator 20 may be pre-strained by 10 to 15%. The amount of pre-strain (ε) may depend on the relationship between the rotating angle (α) and the length of the lever arm ($A_0$) (i.e., the length of the first or second leg 40, 45) using the following equation:

$$\varepsilon = \frac{\Delta L}{L_o}$$

As illustrated in FIG. 1B, for example, to determine the amount to pre-strain the polymer actuator, the following equations may be used.

$$\varepsilon = \frac{L_1 - L_0}{L_0}$$

and $$L_1 = \sqrt{L_0^2 + 2A_0^2 - 2\sqrt{L_0^2 + A_0^2} * A_0 * \cos\left(\alpha + \arctan\left(\frac{L_0}{A_0}\right)\right)}$$

where ε is strain, α is the angle of deflection, $L_0$ is the length of the non-deflected actuator and $L_1$ is the length of the deformed actuator. For example, if $L_0$=8 mm, $A_0$=5 mm, α=8°, $L_1$=8.7 mm are used, ε would be (8.7-8)/(8)=0.087 or 8.7%. By pre-straining, the polymer 20 may deform unidirectionally, for example, lengthwise.

The electro-polymer motor 10 may also comprise a compressible member 55 having a first end 57 and a second end 59. The first end 57 may be fixedly connected to the fixed member 15, and the second end 59 may be fixedly connected to the distal end 46 of the second leg 45. The first and second ends 57 and 59 may be connected to fixed member 15 and second leg 45, respectively, using a variety of known and unknown connection methods and devices, including but not limited to welds, sonic welds, adhesives, seaming technologies, brackets, laminating technologies and methods, combinations thereof, or the like. The compressible member 55 may be spaced apart from the first actuator 20.

Figure 3:
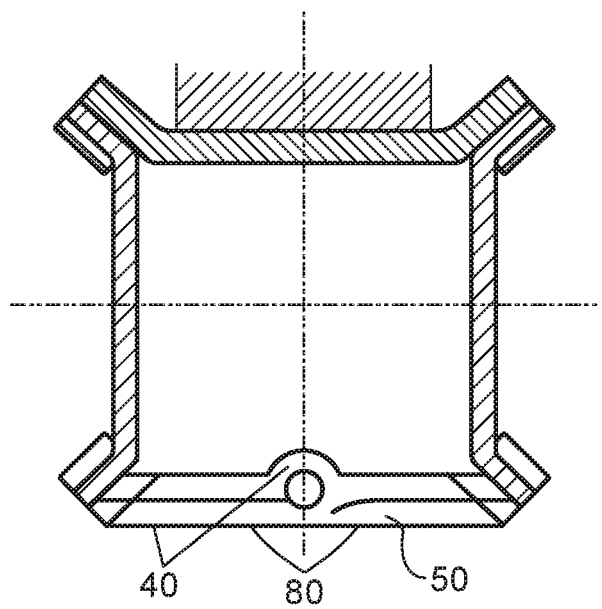
FIG. 3 illustrates a schematic representation of an exemplary electro-polymer motor according to an embodiment of the present invention.

Additionally, as shown in the exemplary embodiments in FIGS. 1-3, the compressible member 55 may be spaced apart from and substantially parallel to the first actuator 20 on an opposite side of the central plane 51. Although, shown connected to the distal end 46 of the second leg 45, it is understood that the compressible member 55 may be connected anywhere along the length and/or width of the second leg 45.

In an exemplary embodiment, the compressible member 55 may comprise a second actuator, as is illustrated in FIG. 1. The second actuator 55 may be comprised of a pre-strained polymer 65 positioned between a pair of electrodes 70, similar to the composition and configuration of the first actuator 20. The pair of electrodes 70 may be also in communication with the power supply (not shown).

When a voltage is applied across the pair of electrodes 30, the first actuator 20 elongates from length $L_0$ to $L_1$ as illustrated in FIGS. 1A and 1B. The deformation of polymer 25, in turn, causes the driven member 35 to move. For example, the elongation of the first actuator 20 may result in the driven member 35 partially rotating about the longitudinal axis 50 in response to the applied voltage (e.g., rotate counter clockwise). When the voltage is unapplied or removed from across the pair of electrodes 30, the polymer may return back to its normal state, i.e., un-deformed state (which may or may not include a pre-strained state). Thus, the returning of the polymer 25 to its normal state may cause the driven member 35 to rotate back the opposite direction about the axis 50 (e.g., clockwise).

In other words, the applying and unapplying of voltage across the pair of electrodes 30 may cause the driven member 35 to oscillate about the longitudinal axis 50. By oscillating, it is meant that the driven member 35 partially rotates back (e.g., counter clockwise) and forth (e.g., clockwise) about the longitudinal axis 50 in response to one or more polymers (e.g., polymer 25) deforming. The polymer(s) may be electrically activated to deform by applying an electrostatic field between the electrodes (e.g., pair of electrodes 30). The polymer 25 may elastically deform in response to the voltage. Additionally, the electrodes (e.g., pair of electrodes 30) may also elastically deform along with the one or more polymers (e.g., polymer 25) in response to the voltage.

The power supply may also alternate power between the first actuator 20 and the second actuator 55 using an oscillating pulse resulting in the driven member 35 rotating and/or oscillating about the longitudinal axis 50. FIG. 4A illustrates an oscillating pulse voltage in a step function that may be delivered to the actuators. Specifically, the power supply may apply a voltage across the pair of electrodes 30 while applying zero voltage across the pair of electrodes 70, and then applying zero voltage to the pair of electrodes 30, while applying a voltage across the pair of electrodes 70. This alternating power may be repeated for any amount of time required to perform a task. Alternatively, FIG. 4B illustrates that an oscillating pulse voltage in a sinusoidal function. The oscillating pulse, in one exemplary embodiment, may apply a positive voltage (the pulse wave above the x-line) to the first actuator 20 while the negative voltage (the pulse wave below the x-line) may be inverted and applied to the second actuator 55.

In one embodiment, the driven member 35 may have an angle of oscillation (α) of about 10 to about 80 degrees about the axis 50. In another embodiment, the driven member 35 may have an angle of oscillation (α) of about 4 to about 60 degrees about the axis 50. In another embodiment, the driven member 35 may have an angle of oscillation (α) of about 2 to about 40 degrees about the axis 50.

Figure 5A:
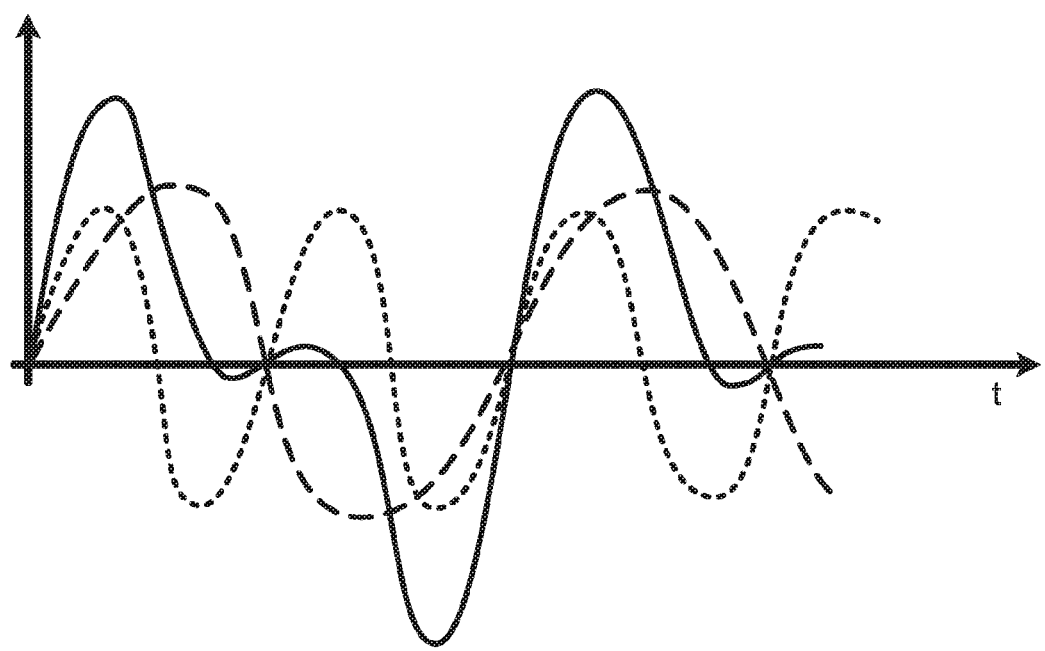
FIG. 5A illustrates an exemplary sinusoid voltage pattern for two different oscillation frequencies according to an embodiment of the present invention.
Figure 5B:
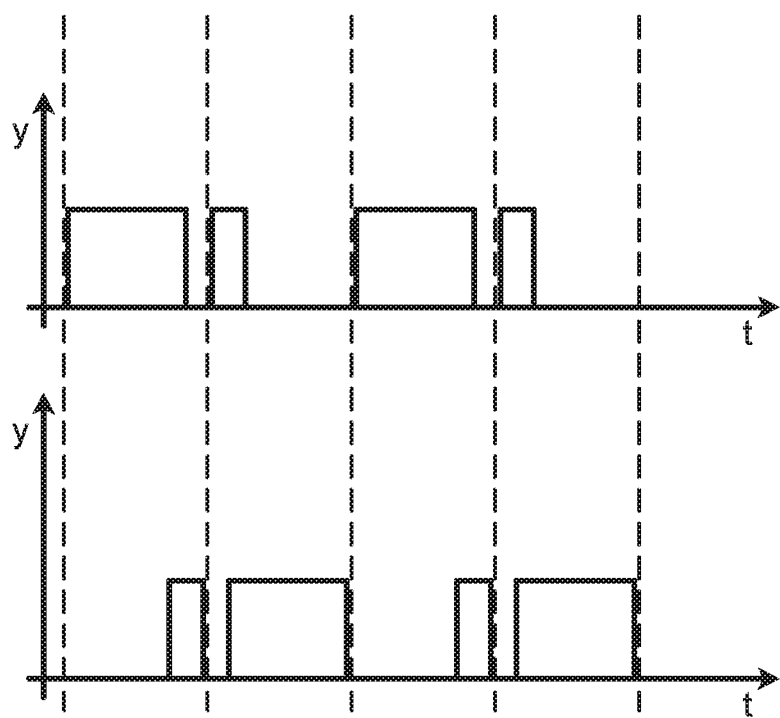
FIG. 5B illustrates an exemplary digital voltage pattern for two different oscillation frequencies according to an embodiment of the present invention.

Alternatively, the power supply may supply substantially concurrent power to the first and second actuators 20, 55 using a pulsating pulse resulting in the driven member moving radially to the axis 50. Again, the pulsating pulse may be sinusoid. Further still, the power supply may supply a substantially concurrent pulsating pulse between the alternating oscillating pulses to produce substantially concurrent oscillating and pulsating motion of the driven member 35 about the axis 50. A controller (not shown) may control the amount of voltage the power supply applies to the pairs of electrodes 30, 70. Additionally, the controller may control the frequency of the pulse pattern. The controller may control the frequency to be between about 0.1 Hz to about 150 kHz, or more specifically between 0.5 Hz to about 100 kHz, and even more specifically between 1 Hz to about 50 kHz. The controller may also overlay the oscillating and pulsating pulse frequencies to produce the substantially concurrent oscillating and pulsating motion of the driven member 35 as shown in FIGS. 5A and B.

Figure 6A:
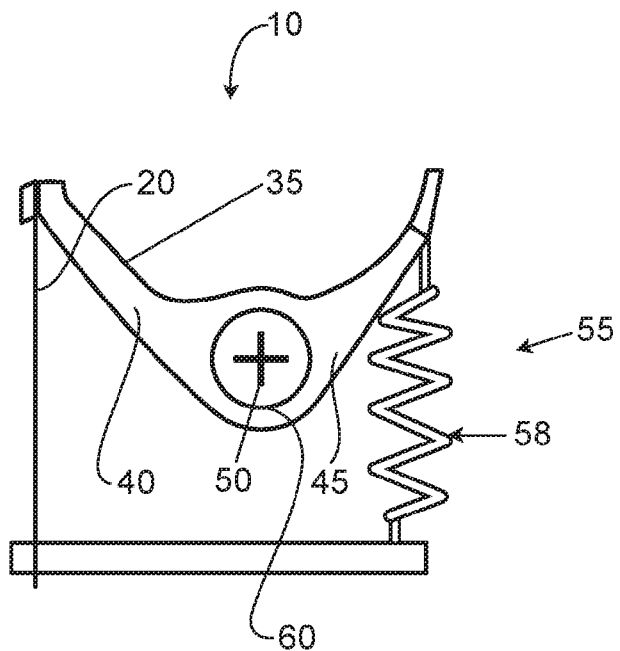
FIG. 6A illustrates a schematic representation of an exemplary electro-polymer motor with one polymer actuator and a spring according to an embodiment of the present invention.
Figure 6B:
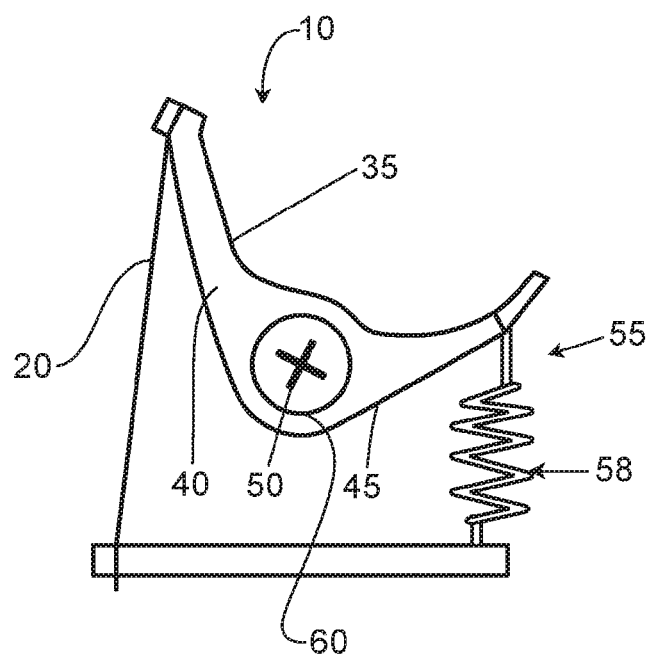
FIG. 6B illustrates a schematic representation of the exemplary electro-polymer motor with one polymer actuator and a spring in a partially rotated representation according to FIG. 6A.
Figure 7:
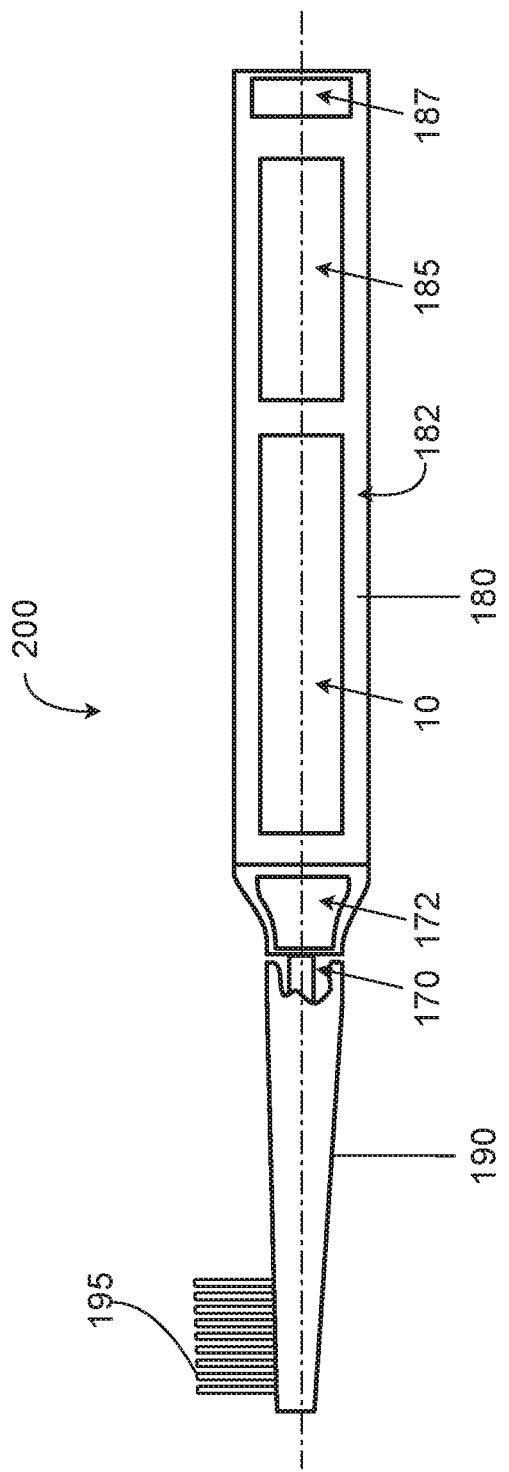
FIG. 7 illustrates a schematic representation of an exemplary toothbrush according to an embodiment of the present invention.

In another exemplary embodiment, the compressible member 55 may be a pre-strained spring 58, as illustrated in FIGS. 6A and 6B. As the first actuator 20 elongates, the spring 58 may be compressed resulting in the driven member 35 to rotate about the longitudinal axis 50 clockwise as shown in FIG. 6B. Again, as set forth above, when the voltage is unapplied across the pair of electrodes 30, the first actuator 20 may return to its original, pre-strained state. As the first actuator 20 returns to its original, pre-strained state, the spring 58 may cause the driven member 35 to rotate about the longitudinal axis 50 back (e.g., counter clockwise) to its original position as shown in FIG. 6A. Thus, the driven member 35 may oscillate about the longitudinal axis 50.

In still another embodiment, a third and fourth actuator (not shown) may be connected between the fixed member 15 and the driven member 35. These actuators may be substantially parallel and proximate to the first actuator 20 and the compressible member 55. Further still, a fifth and sixth actuator (not shown) may be connected between the fixed member 15 and the driven member 35. These actuators also may be substantially parallel and proximate to the first and third actuator 20 and the fourth actuator and the compressible member 55. All the actuators and the compressible member 55 may be separately or substantially concurrently supplied with a voltage across their respective electrodes from the power supply In yet another embodiment, the first actuator 20 may be comprised of two separate actuators positioned side-by-side lengthwise. Likewise, the compressible member 55 may also be comprised of two or more separate actuators positioned side-by-side lengthwise. All the actuators may be separately or substantially concurrently supplied with a voltage across their respective electrodes from the power supply. The power supply may supply oscillating pulses or pulsating pulses to produce rotating, oscillating, pulsating and/or rolling motion.

Referring to FIGS. 7-10, an exemplary embodiment of the electro-polymer motor 10 (as shown in the figures and described herein) in use in a small appliance, such as, for example, an electric toothbrush 200 is illustrated. The electric toothbrush 200 may comprise a head 190 having a cleaning elements 195, a handle 180 connected to the head 190, a seal 172, a motor 10, a drive shaft 170 connecting the motor 10 to either the head 195 and/or the cleaning elements 195, a power supply 185 in communication with the motor 10, a circuit board 182 in communication with the motor 10 and/or the power supply 185, and a charging coil 187. The seal 172, motor 10, drive shaft 170, circuit board 182, power supply 185 and a charging coil 187 may all be disposed within the handle 180.

The toothbrush 200 may comprise any electric toothbrush, electromechanical toothbrush, manual toothbrush, oral cavity surface brush, combinations thereof, or any toothbrush as known to one of ordinary skill in the art. The cleaning elements 195 may comprise bristles, surfaces, elastomers, elastomeric surfaces, foams, combinations thereof, and the like. Some examples of suitable cleaning elements are disclosed in U.S. Patent Application Publication Numbers 2002/0059685; 2005/0000043; 2004/0177462; 2005/0060822; 2004/0154112; U.S. Pat. Nos. 6,151,745; 6,058,541; 6,041,467; 6,553,604; 6,564,416; 6,826,797; 6,993,804; 6,453,497; 6,993,804; 6,041,467; and U.S. patent application Ser. Nos. 12/008,073, filed on Jan. 8, 2008, entitled, "TOOTHBRUSHES" and 60/928,012, filed on May 7, 2007, entitled "ORAL HYGIENE IMPLEMENTS", all of which are herein incorporated by reference in their entirety.

The head 190 and handle 180 may comprise any number of known and unknown shapes, sizes, configurations, and materials. Exemplary materials for the head 190 and handle 180 may include, but not be limited to, polymers, plastics, elastomers, metals, composites, or combinations thereof (e.g., polypropylene, POM, ASA, ABS, PC, SAN, or any other suitable material). The seal 172 may provide a waterproof barrier between the shaft 170 and the handle 180. The seal 172 may protect the motor 10, circuit board 182 and power supply 185 in the handle 180 from the conditions outside the handle 180. The seal 172 may be comprised of a polymer, rubber, or any material known in the art.

The motor 10 may be powered by the power supply 185 and may be operable to provide movement to the head 190 and/or the cleaning elements 195, including but not limited to oscillating, pulsating, and/or linear movement. In this exemplary embodiment, illustrated in FIG. 10, the first actuator and second actuator may each comprise a pre-strained polymer positioned between a pair of electrodes as shown and described above herein. The pair of electrodes of each of the actuators may be in communication with the power supply 185. As such, the first and second actuators are operable to receive voltage from the power supply 185 individually or simultaneously. Additionally, the first actuator and second actuator of the motor 10 may be fixedly connected to the handle 180 at one end of the first and second actuators. Further, the first actuator and second actuator of the motor 10 may be fixedly connected to a driven member 120 at the other end of the first and second actuators.

Figure 8:
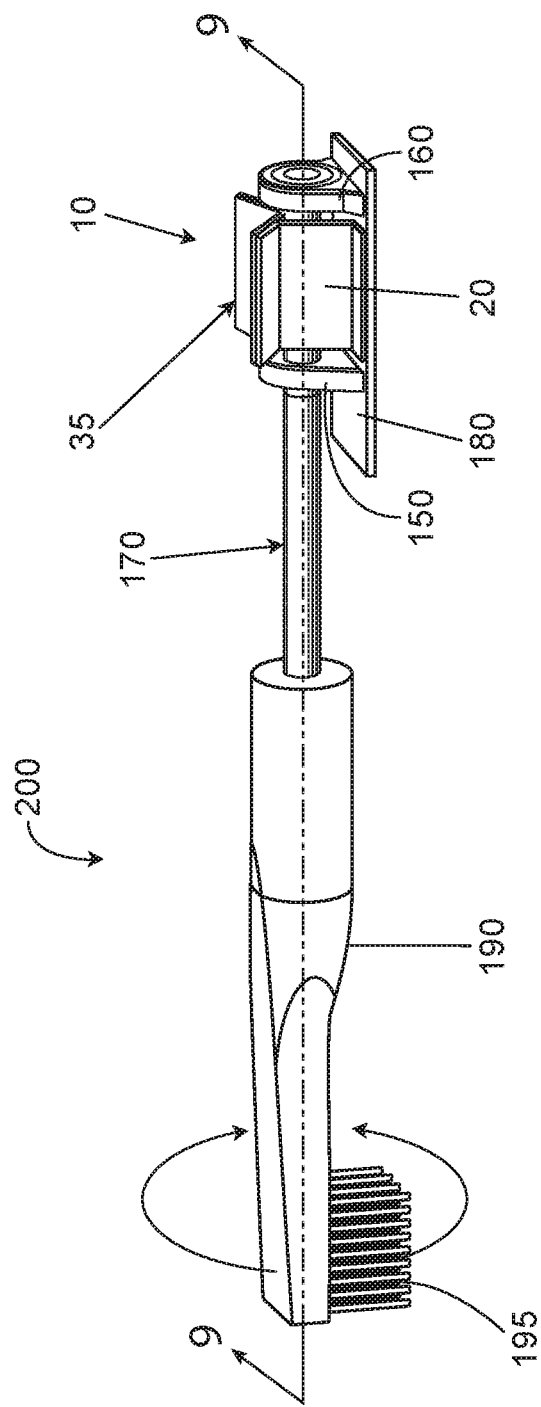
FIG. 8 illustrates a perspective representation of an exemplary drive and driven member of a toothbrush according to an embodiment of the present invention.

The toothbrush 200 may comprise a drive shaft 170 that is in communication with the driven member 120 as illustrated in FIG. 8. In one exemplary embodiment, illustrated in FIG. 10, the drive shaft 170 may be integral with the central body 42 of the motor 10 by sliding and attaching the cylindrical shaped aperture 60 of the motor 10 on to the drive shaft 170 as described herein.

Figure 9:
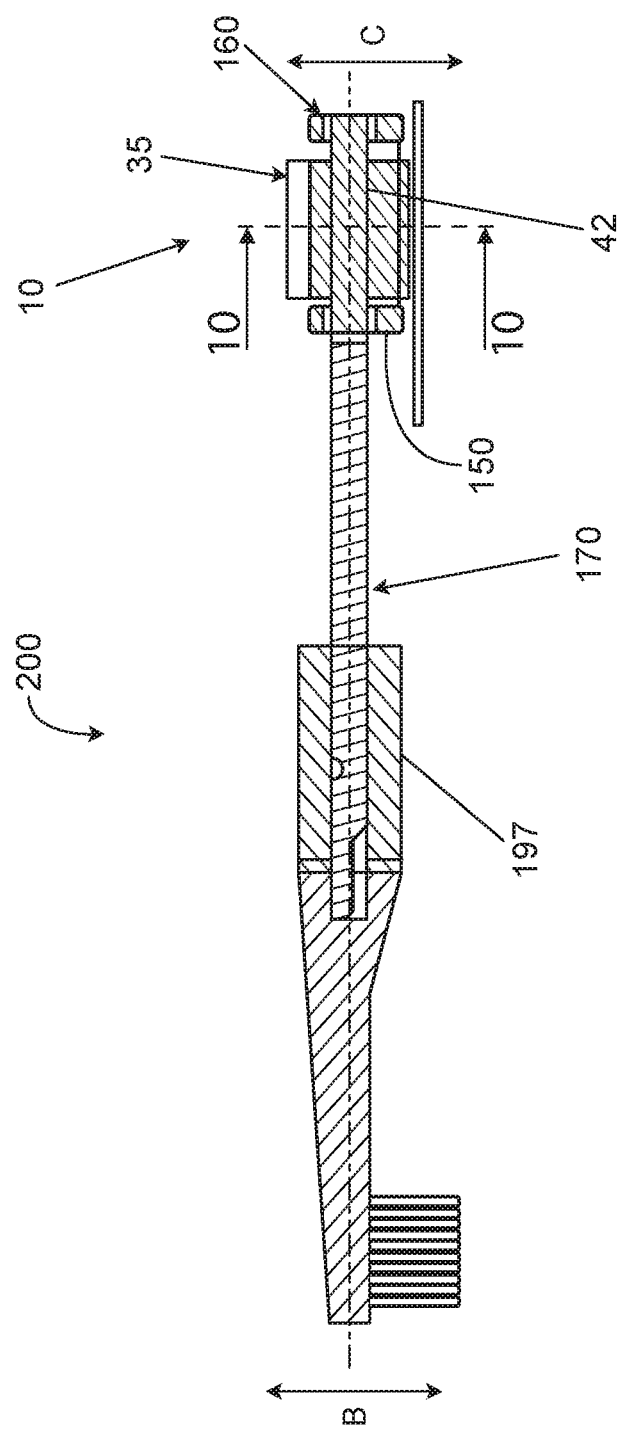
FIG. 9 illustrates a cross-sectional view taken along A-A of the exemplary toothbrush drive system according to FIG. 8.
Figure 10:
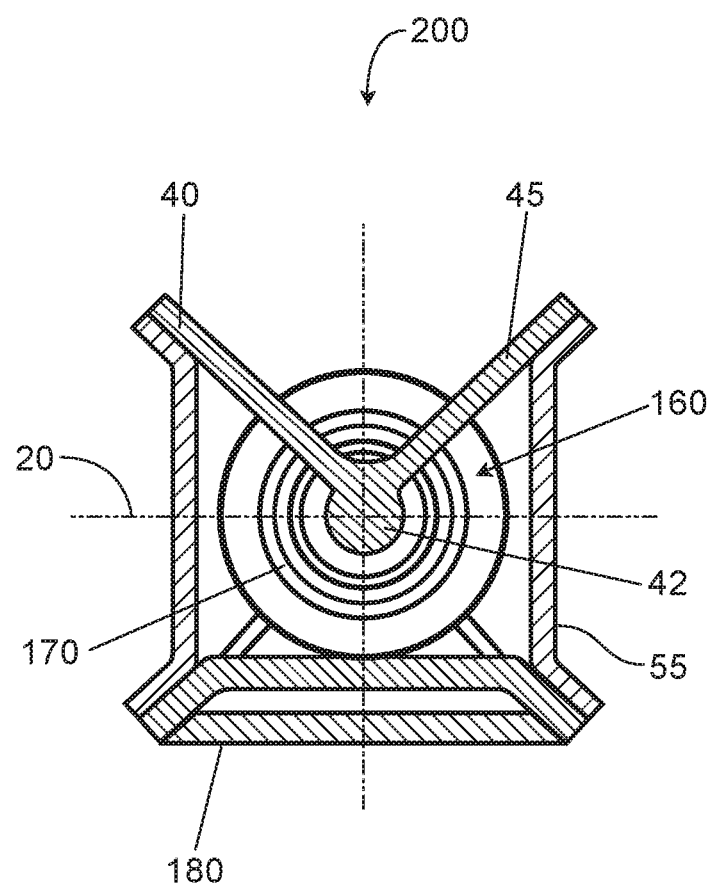
FIG. 10 illustrates a cross-sectional view taken along B-B of the exemplary toothbrush drive system according to FIG. 9.

A cleaning attachment 190 may be in communication with the drive shaft 170 as shown in FIG. 8. In one exemplary embodiment, the cleaning attachment 190 may comprise a head 195 and a neck 197 and may be replaceable as illustrated in FIG. 9. In another exemplary embodiment, just the head 195 of the cleaning attachment 190 may be replaceable. In one exemplary embodiment, the head 195 may comprise cleaning elements for the toothbrush 200 as illustrated in FIG. 8.

Turning back to FIG. 8, the exemplary toothbrush 200 may further comprise a front bearing 150 that may be connected to the handle 180 and the driven member 120 and that may encompassed the drive shaft 170. The front bearing 150 may serve as a pivot point for the drive shaft 170 during pulsating motion. Additionally, the toothbrush 200 may also comprise a back bearing 160 that may be flexible about the drive shaft 170. The back bearing 160 may be flexibly mounted to the handle 180 to permit an alternative or superimposing pivoting motion by the drive shaft 170 about the front bearing 150 during oscillating motion.

The first and second actuators in the toothbrush 200 may elongate in response to an applied voltage from the circuit board 182 to oscillate, pulsate and/or linearly move the driven member 120 and the drive shaft 170. If the circuit board 182 supplies alternates power to the first and second actuators (i.e., sends an oscillating pulse), the drive shaft 170 may oscillates. Alternatively, if the circuit board 182 supplies substantially concurrent power to the first and second actuators (i.e., sends a pulsating pulse), the drive shaft 170 may pulsates. Further, if an oscillating pulse is overlaid with a pulsating pulse, the drive shaft 170 may both oscillate and pulsate.

In one embodiment, the power supply 185 may be a rechargeable battery. In another embodiment, the power supply 185 may be in the form of an A/C adapter. However, any suitable power supply known in the art may be used.

The circuit board 182 may contain the electronic components that comprise a controller and a voltage converter as is well known in the art. The controller as described herein may control the voltage converter as well as the amount of voltage the power supply 185 applies to the electrodes of the motor 10 as well as the frequency of a pulse pattern and the shape of the pulse pattern.

In one exemplary embodiment, the toothbrush 200 may have a switch (not shown) to allow an operator to switch between the drive shaft 170 oscillating, the drive shaft 170 pulsating or the drive shaft 170 oscillating and pulsating concurrently. The switch may be a pushbutton, a toggle switch, or any other suitable type switch known in the art. Alternatively, in another exemplary embodiment, the power supply 185 may switch the type of power supplied to the first and second actuators 110, 112 between the drive shaft 170 oscillating, pulsating or both oscillating and pulsating passed on a predetermined passage of time. For example, the toothbrush 200 may switch the mode of operation to indicate to the operator that the toothbrush 200 should be moved to another quadrant of the mouth or to indicate that a sufficient amount of brushing time has elapsed. The use of electro-polymer motors in small appliances, such as, for example, electric toothbrushes, as shown and described above herein, may have the potential of being more cost-effective, lightweight, consume less power, and smaller.

Figure 11:
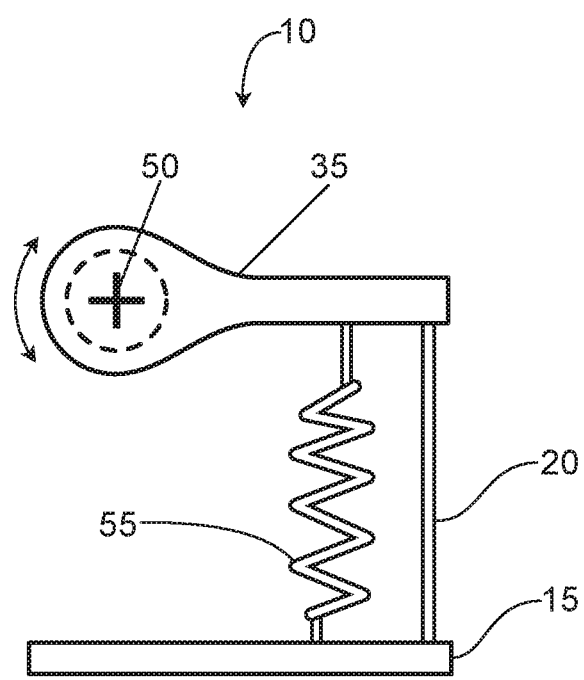
FIG. 11 illustrates another schematic representation of an exemplary electro-polymer motor with one polymer actuator and a spring according to an embodiment of the present invention.

FIG. 11 illustrates another schematic representation of an exemplary electro-polymer motor 10 with one polymer actuator 20 and a spring as the compressible member 55. In this exemplary embodiment, the compressible member 55 may be spaced apart from and substantially parallel to the first actuator 20 on the same side of the longitudinal axis 50 of the driven member 35. The first actuator 20 elongates after a power supply applies a voltage to the first actuator 20 to move the driven member 35 as described above.

Figure 12:
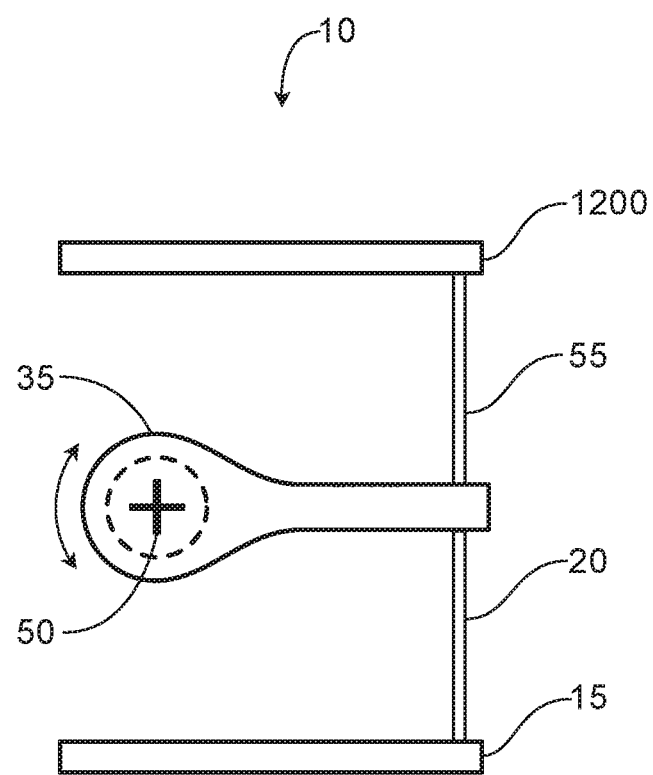
FIG. 12 illustrates another schematic representation of an exemplary electro-polymer motor with two polymer actuators according to an embodiment of the present invention.

FIG. 12 illustrates another schematic representation of an exemplary electro-polymer motor with one polymer actuator 20 and a second actuator as the compressible member 55. In this exemplary embodiment, the second actuator 55 may be spaced apart from and substantially aligned along the same plane of the first actuator 20 on an opposite sides of the driven member 35. Both the first actuator 20 and the second actuator 55 may be positioned on the same side of the longitudinal axis 50 of the driven member 35. The first actuator 20 may be connected to the driven member 35 and a first fixed member 15. The second actuator 55 may be connected to the driven member 35 and a second fixed member 1200. The first actuator 20 elongates after a power supply applies a voltage to the first actuator 20 to move the driven member 35 as described above. Alternatively, a voltage may also be applied to the second actuator 55, substantially concurrently or alternatively, to the voltage that may applied to the first actuator 20.

Figure 13:
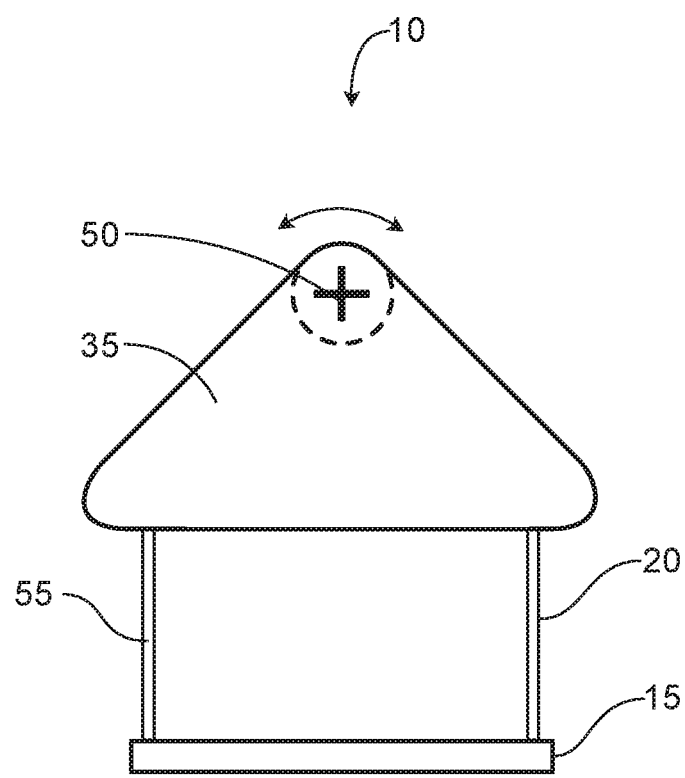
FIG. 13 illustrates still another schematic representation of an exemplary electro-polymer motor with two polymer actuators according to an embodiment of the present invention.

FIG. 13 illustrates still another schematic representation of an exemplary electro-polymer motor with one polymer actuator 20 and a second actuator as the compressible member 55. In this exemplary embodiment, the driven member 35 may be substantially triangular shaped. The first actuator 20 elongates after a power supply applies a voltage to the first actuator 20 to move the driven member 35 as described above. Alternatively, a voltage may also be applied to the second actuator 55, substantially concurrently or alternatively, to the voltage that may applied to the first actuator 20.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

All documents cited in the Detailed Description of the Invention are, in relevant part, incorporated herein by reference; the citation of any document is not to be construed as an admission that it is prior art with respect to the present invention.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. An electric toothbrush, comprising:
a head;
a handle connected to the head;
a power supply; and
a motor, the motor including a fixed member; a first actuator having a first end fixedly connected to the fixed member and a second end, the first actuator comprising a polymer positioned between two electrodes, wherein the electrodes are in communication with a power supply; a driven member comprising a body having cylindrical shape with a cylindrical shaped aperture disposed therethrough, wherein the driven member is fixedly connected to the second end of the first actuator; and wherein the body is disposed longitudinally along a longitudinal axis of the motor and the aperture is coaxially aligned with the longitudinal axis; and a compressible member having a first end fixedly connected to the fixed member and a second end fixedly connected to the body of the driven member, the compressible member spaced apart from the first actuator;

wherein the first actuator changes length after the power supply applies a voltage across the electrodes to move the driven member.

2. An electric toothbrush, the toothbrush comprising:

a head having a cleaning surface;

a handle connected to the head and having a power supply and a motor, wherein the motor comprises:

a first actuator having a first end fixedly connected to the handle and a second end, the first actuator comprises a pre-strained polymer positioned between two electrodes, wherein the electrodes are in communication with the power supply;

a compressible member having a first end fixedly connected to the handle and a second end and spaced apart from and substantially parallel to the first actuator, the compressible member comprises a pre-strained polymer positioned between two electrodes, wherein the electrodes are in communication with the power supply;

a driven member comprising a first leg, a second leg and a shaft bearing positioned between and connected to the first leg and the second leg such that the first leg and the second leg are separated by a first angle across the shaft bearing, the first leg connected to the second end of the first actuator and the second leg connected to the second end of the compressible member; and a shaft in communication with the shaft bearing of the driven member;

wherein the first and second actuators elongate in response to an applied voltage from the power supply to oscillate, pulsate and/or linearly move the driven member and the shaft.

3. The toothbrush according to claim 2, further comprising a cleaning attachment in communication with the shaft.

4. The toothbrush according to claim 3, wherein the cleaning attachment is replaceable.

5. The toothbrush according to claim 2, wherein the power supply alternates power to the first actuator and the compressible member resulting in the shaft oscillating.

6. The toothbrush according to claim 2, wherein the power supply supplies substantially concurrent power to the first actuator and the compressible member resulting in the shaft pulsating.

7. The toothbrush according to claim 2, wherein when the power supply alternates power to the first actuator and the compressible member, the shaft oscillates, and when the power supply supplies substantially concurrent power to the first actuator and the compressible member, the shaft pulsates.

8. The toothbrush according to claim 7, further comprising a switch to select the type of power supplied to the first actuator and the compressible member.

9. The toothbrush according to claim 7, wherein the power supply switches between the type of power supplied to the first actuator and the compressible member based on a time duration.

10. The toothbrush according to claim 2, further comprises a front bearing connected to the handle and the driven member and encompasses the shaft such that the front bearing serves as a pivot point for the shaft.

11. The toothbrush according to claim 10, further comprises a back bearing flexible about the shaft and flexibly mounted to the handle to permit an alternative or superimposing pivoting motion by the shaft about the front bearing.

12. The toothbrush of claim 10 further comprises the front bearing flexible about the shaft and flexibly mounted to the handle to permit an alternative or superimposing pivoting motion by the shaft about a back bearing.

* * * * *